US008883121B2

(12) United States Patent
Inoue et al.

(10) Patent No.: US 8,883,121 B2
(45) Date of Patent: Nov. 11, 2014

(54) ORAL PREPARATION USEFUL IN MEASUREMENT CAPACITY TO METABOLIZE PYRIDINE

(75) Inventors: Yoshiharu Inoue, Tokushima (JP);
Tadashi Mukai, Tokushima (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 1097 days.

(21) Appl. No.: 11/989,286

(22) PCT Filed: Jul. 24, 2006

(86) PCT No.: PCT/JP2006/314591
§ 371 (c)(1),
(2), (4) Date: Jan. 24, 2008

(87) PCT Pub. No.: WO2007/013409
PCT Pub. Date: Feb. 1, 2007

(65) Prior Publication Data
US 2008/0233048 A1    Sep. 25, 2008

(30) Foreign Application Priority Data

Jul. 25, 2005  (JP) .................................. 2005-214762

(51) Int. Cl.
*A61K 49/00* (2006.01)
*A61K 9/16* (2006.01)
*A61K 9/14* (2006.01)
*A61K 9/20* (2006.01)
*A61K 51/12* (2006.01)

(52) U.S. Cl.
CPC .............. *A61K 9/2018* (2013.01); *A61K 9/1623* (2013.01); *A61K 9/145* (2013.01); *A61K 51/1255* (2013.01); *A61K 49/0004* (2013.01)
USPC .......................................................... 424/9.1

(58) Field of Classification Search
None
See application file for complete search history.

(56) References Cited

U.S. PATENT DOCUMENTS

| | | | |
|---|---|---|---|
| 4,451,260 A | 5/1984 | Mitra | |
| 4,830,010 A | 5/1989 | Marshall | |
| 5,233,997 A | 8/1993 | Klein et al. | |
| 5,707,602 A | 1/1998 | Klein | |
| 6,113,875 A | 9/2000 | Nystrom et al. | |
| 6,186,958 B1 | 2/2001 | Katzman et al. | |
| 6,294,151 B1* | 9/2001 | Hayakawa et al. | 424/1.81 |
| 6,509,002 B1 | 1/2003 | Kohno et al. | |
| 6,616,941 B1 | 9/2003 | Seo et al. | |
| 6,740,305 B1 | 5/2004 | Ajami | |
| 7,018,613 B2 | 3/2006 | Nakagawa et al. | |
| 2001/0010825 A1* | 8/2001 | Shimizu et al. | 424/465 |
| 2002/0132283 A1 | 9/2002 | Inada et al. | |
| 2003/0068272 A1* | 4/2003 | Inada et al. | 424/1.81 |
| 2003/0215500 A1* | 11/2003 | Ohta et al. | 424/465 |
| 2004/0234452 A1 | 11/2004 | Inada et al. | |
| 2008/0233048 A1 | 9/2008 | Inoue et al. | |

FOREIGN PATENT DOCUMENTS

| | | |
|---|---|---|
| EP | 0 411 629 A2 | 2/1991 |
| EP | 0 860 170 A1 | 8/1998 |
| EP | 1 374 911 A1 | 1/2004 |
| JP | 46-26989 B1 | 8/1971 |
| JP | 2-172918 A | 7/1990 |
| JP | 3-66613 A | 3/1991 |
| KR | 20010017804 A | 3/2001 |
| WO | WO 91/18105 A1 | 11/1991 |
| WO | WO 96/36330 A2 | 11/1996 |
| WO | WO 97/35622 A1 | 10/1997 |
| WO | WO 9740856 A1 * | 11/1997 |
| WO | WO 98/09658 A1 | 3/1998 |
| WO | WO 00/61197 A1 | 10/2000 |
| WO | WO 02/072153 A1 | 9/2002 |
| WO | WO 2004/87146 A1 | 10/2004 |
| WO | WO 2007/013409 A1 | 2/2007 |

OTHER PUBLICATIONS

Iida et al. J. Labelled Cmpd. Radiopharm. 1997, 39, 69-77.*
Hiroaki Kubo et al., Enhancement of Oral Bioavailability and Pharmacological Effect of 1-(3,4-Dimethmphenyl)-2,3-bis(methoxycarbonyl)-4-hydroxy-6,7,8-trimethoxynaphthalene (TA-7552), a New Hypocholesterolemic Agent, by Micronization in Co-ground Mixture with D-Mannitol, Biological and Pharmaceutical Bulletin, vol. 19, No. 5, 1996, pp. 741-747.
European Search Report dated Jun. 8, 2007 for European Application No. 01925887.0.
European Search Report dated Mar. 23, 2011 for European Application No. 07741475.3.
Braden, B. et al., "$^{13}$C-breath tests: Current State of the Art and Future Directions," *Dig. Liver Dis.* 39(9):795-805 (2007).
Braden, B. et al., "The [$^{13}$C]-Acetate Breath Test Accurately Reflects Gastric Emptying of Liquids in Both Liquid and Semisolid Test Meals," *Gastroenterol.* 108:1048-55 (1995).
Choi, M.G. et al., "Reproducibility and Simplification of $^{13}$C-Octanoic Acid Breath Test for Gastric Emptying of Solids," Am. J. Gastroenterol. 93:92-8 (1998).
Ghoos, Y.F. et al., "Measurement of Gastric Emptying Rate of Solids by Means of a Carbon-Labeled Octanoic Acid Breath Test," *Gastroenterology* 104:1640-7 (1993).
Glerup, H. et al., "Gastric Emptying: A Comparison of Three Methods," *Scand. J. Gastroenterol.* 42:1182-86 (2007).

(Continued)

*Primary Examiner* — Michael G Hartley
*Assistant Examiner* — Sean R Donohue
(74) *Attorney, Agent, or Firm* — Finnegan, Henderson, Farabow, Garrett & Dunner, L.L.P.

(57) ABSTRACT

An object of the present invention is to provide an oral preparation that can be used to diagnose the existence or degree of pyridine metabolic capacity disorder, pyrimidine metabolic rate, etc., with high accuracy and with little variation due to individual differences. The oral preparation is prepared using a powder material obtained by mixing and pulverizing (a) an isotope-labeled compound and/or a pyrimidine metabolite compound and (b) a sugar and/or a sugar alcohol.

12 Claims, 3 Drawing Sheets

(56) References Cited

OTHER PUBLICATIONS

Herting, D.C. et al., "Absorption of Acetic Acid and Glycerol From the Rat Stomach," *Am. J. Physiol.* 187:224-26 (1956).

Inada, M. et al, "Pharmacokinetic modelling of [2-$^{13}$C]Uracil Metabolism in Normal and DPD-Deficient Dogs," *Nucleosides, Nucleotides, and Nucleic Acids* 25:1205-9 (2006).

Inada, M. et al., "Relationships Among Plasma [2-$^{13}$C]Uracil Concentrations, Breath $^{13}$CO$_2$ Expiration, and Dihypropyrimidine Dehydrogenase (DPD) Activity in the Liver in Normal and DPD-Deficient Dogs,"*Drug Metabolism and Disposition* 33(6):381-87 (2005).

Irving, C.S. et al., "[$^{13}$C]bicarbonate kinetics in humans: intra- vs. interindividual variations," *Amer. J. Physiol.* 245(2):R190-R202 (1983).

Ito, S. et al., "Physiologically based pharmacokinetic modelling of the three-step metabolism of pyrimidine using $^{13}$C-uracil as an in vivo probe," *Br. J. Clin. Pharmacol.* 60:584-93 (2005).

*J. Smooth Muscle Res.* (Jpn. Sec.) 6:J-75-J-91 (2002).

*J. Smooth Muscle Res.* (Jpn. Sec.) 6:J-129~J-138 (2002).

Kajiwara, M., "The Breath Test by CO$_2$ Analysis IV. $^{13}$C-Labelled Compounds for the Breath Test," *Radioisotopes*, 41:45-48 (1992).

Karamanolis, G. et al., "Association of the Predominant Symptom With Clinical Characteristics and Pathophysiological Mechanisms in Functional Dyspepsia," *Gastroenterology* 130:296-303 (2006).

Lu, Z. et al., "Decreased Dihydropyrimidine Dehydrogenase Activity in a Population of Patients with Breast Cancer. Implication for 5-Fluorouracil-based Chemotherapy," *Clin. Cancer Res.* 4:325-29 (1998).

Maes, B.D. et al., "$^{13}$C-Octanoic Acid Breath Test for Gastric Emptying Rate of Solids," *Gastroenterol.* 114:856-59 (1998).

Maes, B.D. et al., "Combined Carbon-13-Glycine/Carbon-14-Octanoic Acid Breath Test to Monitor Gastric Emptying Rates of Liquids and Solids," *J. Nuc. Med.* 35(5):824-31 (1994).

Mariani, G. et al., "Radionuclide Gastroesophageal Motor Studies." *J. of Nuc. Med.* 45(6):1004-28 (2004).

Mattison, L.K. et al., "The Uracil Breath Test in the Assessment of Dihydropyrimidine Dehydrogenase Activity: Pharmacokinetic Relationship between Expired $^{13}$CO$_2$ and Plasma [2-$^{13}$C]Dihydrouracil," *J. Am. Assoc. Cancer Res.* 12(2):549-55 (2006).

Meineke, I. et al., "Evaluation of the $^{13}$Co$_2$ Kinetics in Humans After Oral Application of Sodium Bicarbonate as a Model for Breath Testing," *Eur. J. Clin. Invest.* 23(2):91-96 (1993).

Quartero, A.O. et al., "Disturbed Solid-Phase Gastric Emptying in Functional Dyspepsia: A Meta-Analysis," *Dig. Dis. Sci.* 43:2028-33 (1998).

Sanaka, M. et al. "Comparison Between Gastric Scintigraphy and the [$^{13}$C]-Acetate Breath Test with Wagner-Nelson Analysis in Humans," *Clin. Exp. Pharmacol. Physiol.* 33:1239-43 (2006).

Sanaka, M. et al., "The Wagner-Nelson Method Makes the [$^{13}$C]-Breath Test Comparable to Radioscintigraphy in Measuring Gastric Emptying of a Solid/Liquid Mixed Meal in Humans," *Clin. Exp. Pharmacol. Physiol.* 34:641-44 (2007).

Sasaki, Y., Koki Kensa Ni Okero Antei Doitai Riyo, *Nippon Isotope Hoshasen Sogo Kaigi Hobunshu*, 18:610-17 (1988).

Sasaki, Y., "5.1 Use of Stable Isotopes in Clinical Diagnoses," *Kagaku no Ryoiki* 107 "Use of Stable Isotopes in Medicine, Pharmacy and Biology," pp. 149-163 (1975) Nankodo.

Schneider, A.R. et al., "Total Body Metabolism of $^{13}$C-octanoic Acid Is Preserved in Patients with Non-Alcoholic Steatohepatitis, But Differs Between Women and Men," *Eur. J. Gastroenterol. Hepatol.* 17:1181-84 (2005).

Stranghellini, V. et al., "Risk Indicators of Delayed Gastric Emptying of Solids in Patients With Functional Dyspepsia," *Gastroenterol.* 110:1036-42 (1996).

Sugiyama, E. et al., "Desirable Pharmacokinetic Properties of $^{13}$C-uracil as a Breath Test Probe of Gastric Emptying in Comparison with $^{13}$C-acetate and $^{13}$C-octanoate in Rats," *Scand. J. Gastroenterol.* 44:1067-75 (2009).

Tack, J., "Gastric Motor Disorders," *Best Pract. Res. Clin. Gastroenterol.* 21:633-44 (2007).

Talley, n. J. et al., "Functional Gastroduodenal Disorders," *Gut* 45(Suppl II): II37-42 (1999).

Tazawa, S. et al., "KDR-5169, a New Gastrointestinal Prokinetic Agent, Enhances Gastric Contractile and Emptying Activities in Dogs and Rats," *Eur. J. Pharmacol.* 434:169-76 (2002).

Votruba, S.B. et al., "Validation of Deuterium Labeled Fatty Acids for the Measurement of Dietary Fat Oxidation: a Method for Measuring Fat-Oxidation in Free-Living subjects," *Int. J. Obes. Relat Metab. Disord.* 25:1240-45 (2001).

Yen, J.L. at al., "Should DPD Analysis be Required Prior to Prescribing Pluoropyrimidines?" *Eur. J. Cancer* 43:1011-16 (2007).

The Merck Index, Merck Research Laboratories Division of Merck & Co., Inc., 2001, 13th Edition, pp. 1755-1756, 9918. Uracil.

English Abstract of KR 20010017804 A, Mar. 5, 2001, Choi et al.

\* cited by examiner

| 5-FU | : 5-Fluorouracil |
| FDHU | : Fluorodihydrouracil |
| F-β-UPA | : Fluoro-β-ureidopropionic acid |
| F-β-alanine | : Fluoro-β-alanine |
| DPD | : Dihydropyrimidine dehydrogenase |
| DHPase | : Dihydropyrimidinase |
| β-UPase | : β-Ureidopropionase |

ORAL PREPARATION USEFUL IN MEASUREMENT CAPACITY TO METABOLIZE PYRIDINE

TECHNICAL FIELD

The present invention relates to an oral preparation that can be effectively used to assess, with high accuracy, the existence or degree of a pyridine metabolic capacity disorder; pyrimidine-metabolic rate; etc. The present invention also relates to a process for producing the oral preparation.

BACKGROUND ART

5-Fluorouracil (hereinafter sometimes referred to as "5-FU"), various derivatives thereof (such as tegafur, carmofur, doxifluridine, etc.), and like fluorouracil drugs are widely used as anticancer drugs at present. It is known that 5-FU administered to the body is first degraded by the action of dihydropyrimidine dehydrogenase (hereinafter sometimes referred to as "DPD"), which is the first enzyme in the pyrimidine metabolic pathway. It is therefore believed that the concomitant use of a drug that inhibits DPD enzymatic activity is effective in sustaining the effects of fluorouracil drugs such as 5-FU and the like. On the other hand, it is known that when a fluorouracil drug such as 5-FU is administered to a subject with DPD deficiency or reduced DPD activity, the drug is not metabolized in a normal manner and results in an abnormally high fluorouracil drug concentration in the blood, thereby causing severe side effects (e.g., myelosuppression, digestive symptoms, etc).

Thus, in order to effectively exhibit the action of fluorouracil drugs or prevent the side effects of fluorouracil drugs, diagnosis of pyrimidine-metabolic capacity, i.e., the existence, degree, etc., of a pyrimidine metabolic disorder in the subject, before administration of a fluorouracil drug is believed to be important.

A method for diagnosing pyrimidine metabolic activity in a subject has been reported in which an isotope-labeled pyrimidine compound is administered to the subject, and the excretion behavior of the isotope-labeled metabolic product discharged from the body is measured so as to determine the pyrimidine metabolic capacity, i.e., the existence, degree, etc., of a pyrimidine metabolic disorder in the subject (e.g., Patent Document 1). Granules and subtle granules containing isotope-labeled pyrimidine compounds and carriers are already known as pyrimidine metabolic capacity diagnosis preparations for use in the above method.

However, isotope-labeled pyrimidine compounds, such as $^{13}C$-uracil, have, as well as low solubility, characteristically high cohesiveness, although bulk powders of such compounds themselves are fine particles of several microns. Therefore, granules and subtle granules prepared from isotope-labeled pyrimidine compounds as such by standard methods do not rapidly dissolve, and partly because of this, the compounds have disadvantages such as a slow and non-uniform absorption rate in the living body and variation in the absorption rate due to individual differences. Therefore, in order to realize pyrimidine metabolic capacity diagnosis with higher accuracy, it is desired to overcome the above defects so that variation in the excretion time and amount of the isotope-labeled metabolic products can be reduced and the non-uniformity of diagnosis accuracy due to individual differences can be decreased.

Patent Document 1: International Publication No. WO 02/072153, pamphlet

DISCLOSURE OF THE INVENTION

Problems to be Solved by the Invention

An object of the present invention is to provide an oral preparation that can be used to diagnose the existence, degree, etc., of a pyridine metabolic capacity disorder, with high accuracy and with little variation due to individual differences.

Means for Solving the Problems

The present inventors conducted extensive research to solve the above problems, and found that an oral preparation prepared using a powder material obtained by mixing and pulverizing (a) an isotope-labeled compound and/or a metabolite thereof, and (b) a sugar and/or a sugar alcohol, enables pyrimidine metabolic capacity diagnosis with high accuracy and with little variation due to individual differences. The present invention has been achieved by further improvements based on this finding.

The present invention provides the following oral preparations, production processes for the same, etc.

Item 1. An oral preparation produced from a powder material obtained by mixing and pulverizing (a) a pyrimidine compound and/or a metabolite thereof, in which at least one of carbon atoms, oxygen atoms, and nitrogen atoms is labeled with an isotope, and (b) a sugar and/or a sugar alcohol.

Item 2. An oral preparation according to item 1, wherein a particle diameter at 50% of the powder material is 40 μm or less.

Item 3. An oral preparation according to item 1, which contains the component (a) in a proportion of 5 to 20 wt. %.

Item 4. An oral preparation according to item 1, wherein the component (a) is isotope-labeled uracil.

Item 5. An oral preparation according to item 1, wherein the component (b) is mannitol.

Item 6. An oral preparation according to item 1, wherein the component (a) is isotope-labeled uracil and the component (b) is mannitol.

Item 7. An oral preparation according to item 1, which is a granular preparation.

Item 8. An oral preparation according to item 7, which is produced by extrusion granulation of the powder material.

Item 9. An oral preparation according to item 7, wherein the granular preparation has a mean particle diameter of 1400 μm or less.

Item 10. An oral preparation according to item 1, which is a preparation for diagnosing pyrimidine-metabolic capacity.

Item 11. An oral preparation according to item 1, which is a preparation for determining gastric emptying capacity.

Item 12. An oral preparation according to item 1, which is a preparation for diagnosing dyspepsia.

Item 13. A process for producing an oral preparation, the process comprising the steps of:

(1) producing a powder material by mixing and pulverizing (a) a pyrimidine compound and/or a metabolite thereof, in which at least one of carbon atoms, oxygen atoms, and nitrogen atoms is labeled with an isotope, and (b) a sugar and/or a sugar alcohol; and (2) formulating the powder material obtained in the above step (1) into a preparation.

Item 14. A process according to item 13, wherein a particle diameter of the powder material produced in the step (1) is of 40 μm or less.

Item 15. A process according to item 13, wherein the oral preparation contains the component (a) in a proportion of 5 to 20 wt. %.

Item 16. A process according to item 13, wherein the component (a) is isotope-labeled uracil.

Item 17. A process according to item 13, wherein the component (b) is mannitol.

Item 18. A process according to item 13, wherein the component (a) is isotope-labeled uracil and the component (b) is mannitol.

Item 19. A process according to item 13, wherein the oral preparation has a granular form.

Item 20. A process according to item 19, wherein the step (2) is a step of formulating the powder material obtained in the step (1) into a preparation by extrusion granulation.

Item 21. A process according to item 19, wherein the oral preparation is a granular preparation having a mean particle diameter of 1400 μm or less.

Item 22. A process according to item 13, wherein the oral preparation is a preparation for diagnosing pyrimidine metabolic capacity.

Item 23. A process according to item 13, wherein the oral preparation is a preparation for determining gastric emptying capacity.

Item 24. A process according to item 13, wherein the oral preparation is a preparation for diagnosing dyspepsia.

Item 25. Use of a powder material obtained by mixing and pulverizing (a) a pyrimidine compound and/or a metabolite thereof, in which at least one of carbon atoms, oxygen atoms, and nitrogen atoms is labeled with an isotope, and (b) a sugar and/or a sugar alcohol, for producing a preparation for diagnosing pyrimidine metabolic capacity.

Item 26. Use of a powder material obtained by mixing and pulverizing (a) a pyrimidine compound and/or a metabolite thereof, in which at least one of carbon atoms, oxygen atoms, and nitrogen atoms is labeled with an isotope, and (b) a sugar and/or a sugar alcohol, for producing a preparation for determining gastric emptying capacity.

Item 27. Use of a powder material obtained by mixing and pulverizing (a) a pyrimidine compound and/or a metabolite thereof, in which at least one of carbon atoms, oxygen atoms, and nitrogen atoms is labeled with an isotope, and (b) a sugar and/or a sugar alcohol, for producing a preparation for diagnosing dyspepsia.

Effects of the Invention

The oral preparation of the present invention is produced by formulating a powder material obtained by mixing and pulverizing (a) an isotope-labeled compound and/or a metabolite thereof and (b) a sugar and/or a sugar alcohol, into a preparation. With such formulation, the oral preparation of the present invention makes it possible to diagnose pyrimidine metabolic capacity and gastric emptying capacity with high accuracy and with little variation due to individual differences. As a result, the behavior of an isotope-labeled metabolic product can be correctly determined by one or a small number of measurements, 20 to 30 minutes after administration of the preparation, so that the time required for the determination and the number of measurements can be reduced, thereby decreasing the burden on patients.

BEST MODE FOR CARRYING OUT THE INVENTION

Figure 1:
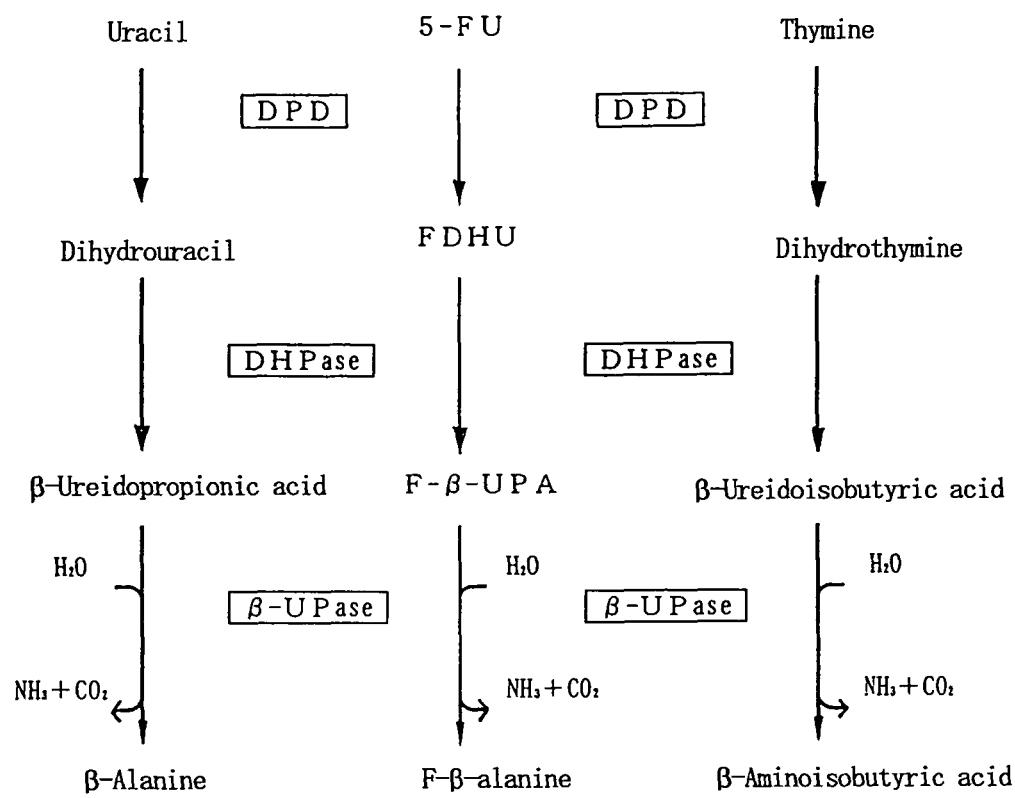
[FIG. 1] A figure showing the behavior of degradation (metabolism) of pyrimidine compounds (uracil, 5-fluorouracil (5-FU), and thymine) by a series of pyrimidine metabolizing enzymes (dihydropyrimidine dehydrogenase (DPD), dihydropyrimidinase (DHPase), and β-ureidopropionase (β-UPase)).

The present invention is described below in detail.

The oral preparation of the present invention contains an isotope-labeled pyrimidine compound and/or a metabolite thereof (hereinafter these are sometimes referred to as "Component (a)").

The pyrimidine compound for use in the present invention may be any of a wide variety of compounds having a pyrimidine skeleton, and is preferably a compound that serves as a substrate for a pyrimidine metabolizing enzyme, and in particular dihydropyrimidine dehydrogenase (DPD), which is the first enzyme in the pyrimidine metabolic pathway in the living body. Specific examples of such pyrimidine compounds include uracil, thymine, and derivatives thereof. The derivatives of uracil and thymine are not limited as long as they serve as substrates for DPD, and as long as their final metabolic products formed via the pyrimidine metabolic pathway are discharged in excrement such as expired air, urine, or sweat. Specific examples of such derivatives include halides of uracil, such as 5-fluorouracil, 5-bromouracil, etc.; halides of thymine, such as 5-fluorothymine, 5-bromothymine, etc.; and the like. Preferable examples of pyrimidine compounds include uracil, thymine, and 5-fluorouracil.

Usable pyrimidine compounds include, in addition to the above compounds, which serve as direct substrates for DPD, compounds that serve as indirect substrates for the enzyme, i.e., precursors (including prodrugs), which are metabolized or degraded in vivo into substrates for DPD (such as uracil, thymine, 5-fluorouracil, etc.). Examples of such precursors include precursors of uracil, such as cytosine, uridine, and phosphates thereof (e.g., uridylic acid); precursors of thymine, such as 5-methylcytosine, thymidine, and phosphates thereof (e.g., thymidylic acid); and precursors (prodrugs) of 5-fluorouracil, such as tegafur, carmofur, doxifluridine, etc.

The metabolite of a pyrimidine compound is a compound that corresponds to a metabolic intermediate of the pyrimidine compound and that serves as a substrate for a pyrimidine metabolizing enzyme, and in particular dihydropyrimidinase (hereinafter sometimes referred to as "DHPase"), which is the second enzyme in the pyrimidine metabolic pathway in the living body, or β-ureidopropionase (hereinafter sometimes referred to as "β-UPase"), which is the third enzyme. Specific examples of metabolites of pyrimidine compounds include dihydrouracil, dihydrothymine, and derivatives thereof (e.g., halides of dihydrouracil, such as 5-fluorodihydrouracil and the like), which serve as substrates for DHPase; and β-ureidopropionic acid, β-ureidoisobutyric acid, and derivatives thereof (e.g., halides of β-ureidopropionic acid, such as fluoro-β-ureidopropionic acid, and halides of β-ureidoisobutyric acid), which serve as substrates for β-UPase.

In the present invention, Component (a) is preferably a pyrimidine compound, more preferably uracil, thymine, or 5-fluorouracil, and still more preferably 5-fluorouracil.

In the pyrimidine compound and/or metabolite thereof for use in the present invention, at least one of the carbon atoms, oxygen atoms, and nitrogen atoms in the molecule is labeled with an isotope. The isotope is not limited, and specific examples include $^{13}C$, $^{14}C$, $^{18}O$, and $^{15}N$. The isotope may be radioactive or non-radioactive, but $^{13}C$, $^{18}O$, or $^{15}N$, which are non-radioactive, are preferable from the viewpoint of safety.

The pyrimidine compound and/or metabolite thereof for use in the present invention may have one isotope in the molecule or may have two or more isotopes of the same or different elements. Although not limitative, it is preferable that a carbon atom or oxygen atom in the pyrimidine compound or metabolite thereof be labeled so that at least part (C or O) of $CO_2$ produced via the pyrimidine metabolic pathway is labeled with an isotope. Examples of such pyrimidine compounds include those having an isotope-labeled carbon atom at the 2-position of the pyrimidine skeleton. Specific examples include 2-$^{13}C$-labeled uracil and 2-$^{13}C$-labeled fluorouracil.

The method for labeling a pyrimidine compound and/or a metabolite thereof with an isotope as mentioned above is not limited, and a wide variety of conventional methods can be employed (Sasaki, "5.1 Application of Stable Isotopes in Clinical Diagnosis"; Kagaku no Ryoiki (Journal of Japanese Chemistry) 107, "Application of Stable Isotopes in Medicine, Pharmacy, and Biology", Nankodo, pp. 149-163 (1975); Kajiwara, "RADIOISOTOPES", 41, 45-48 (1992); etc.). Some of such isotope-labeled pyrimidine compounds and metabolites thereof are commercially available, and these commercial products are conveniently usable.

The proportion of Component (a) in the oral preparation of the present invention is, for example, usually 5 to 20 wt. %, preferably 6 to 18 wt. %, and more preferably 8 to 15 wt. %.

The oral preparation of the present invention contains, in addition to Component (a), a sugar and/or a sugar alcohol (hereinafter these are sometimes referred to as "Component (b)").

The sugar for use in the present invention is not limited as long as it is pharmaceutically acceptable. Examples of such sugars include glucose, galactose, fructose, xylose, arabinose, mannose, and like monosaccharides; maltose, isomaltose, cellobiose, lactose, sucrose, trehalose, and like disaccharides; etc. Among these, glucose and sucrose are preferable.

The sugar alcohol for use in the present invention is not limited as long as it is pharmaceutically acceptable.

Specific examples of sugar alcohols include erythritol, mannitol, xylitol, sorbitol, maltitol, reducing paratinose, lactitol, etc. Among these, mannitol, xylitol, and erythritol are preferable, and mannitol is more preferable.

In the present invention, Component (b) is preferably a sugar alcohol, more preferably mannitol, xylitol, or erythritol, and still more preferably mannitol.

The proportion of Component (b) in the oral preparation of the present invention is, for example, usually 80 to 95 wt. %, preferably 82 to 94 wt. %, and more preferably 85 to 92 wt. %, based on the total weight of the preparation.

The ratio of Component (b) to Component (a) in the oral preparation of the present invention is, for example, 400 to 1900 parts by weight, preferably 450 to 1550 parts by weight, and more preferably 550 to 1150 parts by weight, of Component (b), per 100 parts by weight of Component (a). The combined use of Components (a) and (b) in such a ratio further improves the accuracy of pyrimidine metabolic disorder diagnosis.

The oral preparation of the present invention is produced by formulating a powder material containing Components (a) and (b) into a preparation. The powder material used for preparing the oral preparation of the present invention is obtained by mixing Components (a) and (b) in the above ratio and pulverizing the resulting mixture.

The oral preparation of the present invention may have the same composition as the powder material after pulverization, or may contain other components in addition to the powder material. Therefore, the proportions of Components (a) and (b) in the powder material are suitably selected according to the proportions of Components (a) and (b) in the final form of the oral preparation, the preparation steps for the oral preparation, etc.

The powder material may be obtained by mixing and pulverizing pharmaceutically acceptable additives together with Components (a) and (b), as long as the effects of the present invention are not impaired. Such additives are the same as those that can be added when formulating the powder material into a preparation. Specific examples of such additives are given hereinafter.

The particle diameter of the powder material is not limited as long as the particle diameter is a result from mixing and pulverizing Components (a) and (b), but in order to increase the accuracy of pyrimidine metabolic capacity diagnosis, it is desirable that the particle diameter at 50% be 40 μm or less, preferably 30 μm or less, and more preferably 5 to 20 μm.

Preferable examples of the powder material are powder materials having a particle size distribution such that the particle diameter at 50% is 40 μm or less and the particle diameter at 90% is 200 μm or less; more preferable examples are those having a particle size distribution such that the particle diameter at 50% is 30 μm or less, and the particle diameter at 90% is 100 μm or less; and still more preferable examples are those having a particle size distribution such that the particle diameter at 50% is 5 to 20 μm, and the particle diameter at 90% is 10 to 70 μm. Use of a powder material having such particle size distribution to prepare the oral preparation enables Component (a) to be absorbed in the living body at a rapid and uniform rate, thereby making it possible to diagnose pyrimidine metabolic capacity with higher accuracy.

As used herein, the meanings of the particle diameter at 50% and particle diameter at 90% of the powder material are as follows: the volume of the particles of the powder material is integrated in order from the particle with the smallest particle diameter, until the integrated volume accounts for 50% or 90% of the total volume of the particles of the powder material, and the particle diameter of the last particle integrated is the particle diameter at 50% or 90%. The particle diameter at 50% and particle diameter at 90% can be measured using a dry laser method (measurement conditions: a focal distance of 100 mm, a number of averaging processes of 10, an averaging interval of 5 milliseconds, and an air pressure of 0.4 MPa).

The pulverizing treatment used for the preparation of the powder material is not limited, but pulverizing treatment using a dry mill is preferable. Specific examples of dry mills include hammer mills, pin mills, jet mills, etc.

The oral preparation of the present invention is produced by adding, as required, additives such as excipients, binders, pH adjusters, disintegrators, absorption enhancers, lubricants, colorants, corrigents, flavors, etc., to the powder material, and formulating the resulting mixture into a preparation via a treatment such as granulation or another forming procedure, which is selected according to the form of the preparation. When the oral preparation of the present invention is a powder preparation, the powder material as such can be used as the oral preparation in the final form.

Specific examples of additives that can be used for formulation include lactose, starch, refined white sugar, dextrin, mannitol, xylitol, sorbitol, erythritol, calcium dihydrogen phosphate, sodium chloride, glucose, calcium carbonate, kaolin, crystalline cellulose, silicate, and like excipients; water, ethanol, simple syrup, glucose solutions, starch solutions, gelatin solutions, carboxymethylcellulose, carboxymethylcellulose sodium, shellac, methylcellulose, hydroxypropylmethylcellulose, hydroxypropylcellulose, polyvinylpyrrolidone, polyvinyl alcohol, gelatin, dextrin, pullulan, and like binders; citric acid, citric anhydride, sodium citrate, sodium citrate dihydrate, anhydrous sodium monohydrogen phosphate, anhydrous sodium dihydrogen phosphate, sodium hydrogen phosphate, anhydrous sodium dihydrogen phosphate, and like pH adjusters; carmellose calcium, low-substituted hydroxypropycellulose, carmellose, croscarmellose sodium, carboxymethyl starch sodium, crospovidone, and like disintegrators; polysorbate 80, quaternary ammonium bases, sodium lauryl sulfate, and like absorption enhancers; purified talc, stearate, polyethylene glycol, colloidal silicic acid, sucrose fatty acids, hydrogenated oils, and like lubricants; yellow iron oxide, yellow iron sesquioxide, iron sesquioxide, β-carotene, titanium oxide, food colors (e.g., Food Blue No. 1), copper chlorophyll, riboflavin, and like colorants; ascorbic acid, aspartame, sweet hydrangea leaf, sodium chloride, and like corrigents; and the like.

The form of the oral preparation of the present invention is not limited as long as it is a solid preparation, and subtle granules, granules, powders, tablets (including naked tablets and coated tablets), capsules, pills, and other forms can be selected as desired. Among these, to further enhance the effects of the present invention, granular preparations such as subtle granules and granules, and in particular granular preparations produced by extrusion granulation, are preferred.

When the oral preparation of the present invention is a granular preparation, the mean particle diameter of the preparation is, for example, usually 1400 μm or less, preferably 50 to 1200 μm, and more preferably 100 to 1000 μm. When the granular preparation has such a particle diameter, the granular preparation enables pyrimidine metabolic capacity diagnosis with higher accuracy. The particle diameter of the preparation can be measured using a vibration sieve method (specifically, using a measurement apparatus Robot Shifter RPS-95 (Seishin Enterprise Co., Ltd.) at a vibration level of 5, a shift time of 5 minutes, and a pulse interval of 1 second).

After administering the oral preparation of the present invention, the pyrimidine metabolic capacity, i.e., the existence or degree of a pyrimidine metabolic disorder, pyrimidine metabolic rate, etc., in a subject, can be assessed by measuring the excretion behavior of the isotope-labeled metabolic product excreted from the body. Therefore, the oral preparation of the present invention can be used as a preparation for determining pyrimidine metabolic capacity. Further, as described hereinafter, since gastric emptying capacity can also be assessed based on the assessment results of pyrimidine metabolic capacity, and specifically the results of measuring pyrimidine metabolic rate, the oral preparation of the present invention can also be used as a preparation for determining gastric emptying capacity. Embodiments of the preparation for determining pyrimidine metabolic capacity and the preparation for determining gastric emptying capacity are specifically described below.

Preparation for Determining Pyrimidine Metabolic Capacity

Since the oral preparation of the present invention can be used to determine pyrimidine metabolic capacity with respect to the existence, degree, etc., of a pyrimidine metabolic disorder, the preparation is useful for the detection, measurement, and diagnosis of a pyrimidine metabolic disorder. Specific conditions, method, etc., for using the oral preparation of the present invention as a preparation for determining pyrimidine metabolic capacity are as follows.

When the oral preparation of the present invention is administered to a subject with normal pyrimidine metabolic capacity, in whom or which the series of pyrimidine metabolizing enzymes (DPD, DPHase, and β-UPase) function normally in the living body (hereinafter sometimes referred to as a "healthy subject"), the pyrimidine compound contained as Component (a) in the preparation is metabolically degraded into metabolic products such as β-alanine, F-β-alanine, β-aminoisobutyric acid, $NH_3$, $CO_2$, etc., as shown in FIG. 1.

The final metabolic product $CO_2$ thus formed by metabolism is excreted in expired air, and β-alanine, F-β-alanine, or β-aminoisobutyric acid is excreted mainly in urine. Of the final metabolic products thus excreted, at least one of $CO_2$ and a final metabolic product selected from β-alanine, F-β-alanine, and β-aminoisobutyric acid is labeled with an isotope, depending on the isotope-labeled site of the pyrimidine compound and/or metabolite thereof used as Component (a). Such an isotope label is used as an index to measure the excretion behavior (the behavior of excretion amount or excretion rate over time) of these final metabolic products using, as a test sample, expired air when $CO_2$ is labeled, or urine when β-alanine, F-β-alanine, β-aminoisobutyric acid, or ammonia is labeled.

The pyrimidine metabolic capacity of the subject can be determined from the thus measured excretion behavior (the behavior of excretion amount or excretion rate over time) of the isotope-labeled metabolic product.

When the oral preparation of the present invention is used for determining pyrimidine metabolic capacity, the dose of the oral preparation of the present invention is not limited, but is preferably an amount corresponding to 1 to 2000 mg, and preferably 10 to 300 mg, of Component (a).

When using the oral preparation of the present invention for determining pyrimidine metabolic capacity, it is preferable to use as Component (a) a pyrimidine compound and/or a metabolite thereof that causes isotope-labeled $CO_2$ to be excreted in expired air as a result of metabolism. Using such a preparation, the pyrimidine metabolic capacity of a subject can be determined from the excretion behavior (the behavior of excretion amount and excretion rate over time) of isotope-labeled $CO_2$, which can be found by administering the preparation to the subject and measuring isotope-labeled $CO_2$ excreted in the expired air of the subject.

When the preparation contains, as an active ingredient, a pyrimidine compound that forms an isotope-labeled compound other than isotope-labeled $CO_2$, such as β-alanine, fluoro-β-alanine, β-aminoisobutyric acid, or the like, excrement such as urine, sweat or the like is used in place of expired air as a test sample.

When expired air is used as a test sample, the method for measuring isotope-labeled $CO_2$ contained in expired air varies depending on whether the isotope used is radioactive or non-radioactive. Conventional analytic methods are usable, including a liquid scintillation-counter method, mass spectrometry, infrared spectrometry, emission spectrometry, magnetic resonance spectrometry, etc. From the viewpoint of measurement accuracy, infrared spectrometry and mass spectrometry are preferable. When excrement such as urine, sweat, or the like is used as the test sample, the isotope-labeled pyrimidine compound (or an isotope-labeled pyrimidine metabolite), isotope-labeled metabolic intermediates, and isotope-labeled metabolic products contained in the test sample can be separated simultaneously and analyzed at the same time by the combined use of separation techniques, such as liquid chromatography, gas chromatography, etc. Thus, the excretion behavior of the isotope-labeled metabolites can be selectively measured.

The pyrimidine metabolic capacity in a subject can be assessed by, for example, comparing the excretion behavior (the behavior of the excretion amount or excretion rate over time) of an isotope-labeled metabolic product in the subject, which is measured as described above, with the excretion behavior of the isotope-labeled metabolic product in a healthy subject having a normal pyrimidine metabolic capacity, which is measured in the same manner. Specifically, when isotope-labeled $CO_2$ excreted in expired air is measured as an isotope-labeled metabolic product, the amount of isotope-labeled $CO_2$ gas at a predetermined time after administration of the oral preparation, carbon dioxide gas Δ (‰) value (difference in the isotope-labeled $^{13}CO_2/^{12}CO_2$ concentration ratio between the expired air samples collected before and after administration of the oral preparation), or the initial rate of isotope-labeled $CO_2$ gas excreted rate in expired air, can be used as an index of the excretion behavior of the isotope-labeled metabolic product. For example, using the carbon dioxide gas Δ (‰) value or initial rate in a healthy subject as a standard, a subject having a lower carbon dioxide gas Δ (‰) value or lower initial rate is diagnosed as having reduced pyrimidine metabolic capacity.

Further, in place of or in addition to the excretion behavior of an isotope-labeled metabolic product, the area under the curve (AUC), excretion rate (especially the initial excretion rate), maximum excretion concentration (Cmax), or like parameter, preferably a pharmacokinetic parameter, in a test subject, can be compared with the corresponding parameter in a healthy subject.

The deficiency or existence of a pyrimidine metabolizing enzyme (at least one of DPD, DHPase, and β-UPase) can be determined based on the existence or non-existence of the excretion of the isotope-labeled metabolic product, without comparison with the excretion behavior of a healthy subject. The existence of a decrease or increase in pyrimidine metabolic capacity (pyrimidine metabolic disorder), and the degree thereof (degree of the disorder) can be determined by comparing the excretion behavior in the subject or a parameter obtained therefrom, with the corresponding excretion behavior or parameter in a healthy subject.

Preparation for Determining Gastric Emptying Capacity

When using the oral preparation of the present invention for determining gastric emptying capacity, it is preferable to use as Component (a) a pyrimidine compound and/or a metabolite thereof that causes isotope-labeled $CO_2$ to be excreted in expired air as a result of metabolism.

After being orally ingested by a subject, the oral preparation of the present invention enters the stomach, and is finally discharged through the pylorus by the contraction-relaxation and peristalsis of the stomach. After being discharged from the pylorus, Component (a) is rapidly absorbed in the duodenum and lower parts of the gastrointestinal tract (the duodenum, jejunum, ileum, etc.), metabolized, and excreted in expired air as isotope-labeled $CO_2$ gas. Component (a) used in the oral preparation of the present invention is not at all or hardly absorbed in the stomach, but after being discharged from the stomach, the component is rapidly absorbed, metabolized, and excreted in expired air as isotope-labeled $CO_2$ gas. Therefore, the excretion behavior of isotope-labeled $CO_2$ gas in expired air (expressed as, for example, a ratio of isotope-labeled $CO_2$ gas relative to $^{12}CO_2$ excreted in the expired air (isotope-labeled $CO_2/^{12}CO_2$)) depends on the gastric emptying rate (gastric emptying time) of Component (a) contained in the oral preparation of the present invention.

The dose of the oral preparation of the present invention may be the same as in the case where the oral preparation of the present invention is used for determining pyrimidine metabolic capacity.

Isotope-labeled $CO_2$ contained in expired air can be measured using the same method as in the case where the oral preparation of the present invention is used for determining pyrimidine metabolic capacity.

The gastric emptying capacity in a subject can be assessed using, as a gastric emptying capacity index, the amount of isotope-labeled $CO_2$ gas at a predetermined time after administration of the oral preparation, the carbon dioxide gas Δ (‰) value (difference in the isotope-labeled $CO_2/^{12}CO_2$ concentration ratio between expired air samples collected before and after administration of the oral preparation), or initial rate of isotope-labeled $CO_2$ gas excreted rate. For example, using the carbon dioxide gas Δ (‰) value or initial rate in a healthy subject as a standard, a subject having a lower carbon dioxide gas Δ (‰) value or initial rate can be diagnosed as having reduced gastric emptying capacity.

The oral preparation of the present invention can be administered singly, or may be administered at the same time as or immediately before or after ingestion of a test meal. Preferably, the gastric emptying capacity-determining composition of the present invention is administered immediately after ingestion of a test meal. The test meal is not limited as long as it does not impair the effects of the gastric emptying capacity determination using the preparation of the present invention, and may be a solid food, fluid food, or liquid food.

The main cause of dyspepsia (non-ulcer upper gastrointestinal tract syndrome) is a gastrointestinal motility disorder, and in particular reduction of gastric emptying capacity. Therefore, the oral preparation of the present invention can be effectively used as a preparation for a diagnostic test for dyspepsia, and in particular dyspepsia caused mainly by insufficient gastric emptying capacity (e.g., dysmotility-like dyspepsia).

Further, use of the oral preparation of the present invention for determining gastric emptying capacity makes it possible to determine the efficacy, or the therapeutic effects on individual subjects, of gastrointestinal drugs, and in particular drugs associated with gastrointestinal motor functions. Specifically, the determination can be performed by measuring the gastric emptying capacity using the oral preparation of the present invention before and after administration of a gastrointestinal drug, and in particular a drug associated with gastric mobility function, and comparing the two measurements. This assesses the efficacy of the drug itself. In addition, since therapeutic effects of a drug on individual subjects can also be assessed, the oral preparation can also be used for selecting drugs that are suitable for individual subjects. Examples of drugs associated with gastrointestinal motor functions include drugs that control the peristalsis of the stomach by enhancement or suppression, such as gastrointestinal motor function improving agents, gastrointestinal motor function enhancers, and gastrointestinal motor function activators (specifically, acetylcholine agonists, dopamine receptor antagonists, dopamine $D_2$ receptor antagonists, serotonin receptor agonists, opiate agonists, and Chinese medicines (Liu Jun Zi Tang, Ban Xia Xie Xin Tang, and An Zhong San), and gastrointestinal motor function suppressants (anticholinergic drugs, muscarinic receptor antagonists, etc.), and the like. Such determination can also be performed on a dyspeptic patient, and in particular a patient with dyspepsia caused mainly by insufficient gastric motor functions (a patient with dysmotility-like dyspepsia), as a test subject. In this case, the pharmacotherapeutic effects on individual dyspepsia patients can be determined, thereby making it possible to select a suitable drug associated with gastrointestinal motor functions (a gastrointestinal motor function improving agent, gastrointestinal motor function enhancer, or gastrointestinal motor function activator as mentioned above).

EXAMPLES

The present invention is described below with reference to Examples and Test Examples, which show production examples and evaluations of the properties of preparations. However, the scope of the present invention is not limited to these Examples and Test Examples.

Production Examples of Preparations

Example 1

Twenty grams of $^{13}$C uracil and 380 g of D-mannitol (Mannit, a product of Kyowa Hakko Kogyo Co., Ltd.) were mixed, placed into a sample mill (KIIWG-1F, a product of Fuji Paudal Co., Ltd.), and mixed and pulverized (pulverization conditions: at a pulverization rotor speed of 12800 rpm and a sample feed motor speed of about 10 rpm, using a screen with 1-mm diameter punched holes), to prepare a powder material. A 200-g quantity of the obtained powder material was weighed out into a speed kneader (NSK-150, a product of Okada Seiko Co., Ltd.), and 20 g of purified water was added, followed by kneading. The resulting wet powder was extruded through an extrusion granulator (Dome Gran DG-L, a product of Fuji Paudal Co., Ltd.) equipped with a dome-shaped die with 1-mm diameter holes, and dried using an air-blow dryer (SPHH-200, a product of Espec Corp.) set at 60° C. Among the particles of the dried preparation, those that passed through a sieve having a mesh size of 1400 μm and did not pass through a sieve having a mesh size of 355 μm were obtained as a granular preparation containing 5 wt. % of $^{13}$C uracil.

The particle diameter of the thus obtained granular preparation containing 5 wt. % of $^{13}$C uracil was measured by a vibration sieve method (specifically, using a Robot Shifter RPS-85 measurement apparatus (a product of Seishin Enterprise Co., Ltd.) at a vibration level of 5, a shift time of 5 minutes, and a pulse interval of 1 second). Table 1 shows the results.

TABLE 1

| Particle Diameter | Proportion (wt. %) |
|---|---|
| 1400 μm or more | 2.09 |
| Not less than 1000 μm and less than 1400 μm | 7.29 |
| Not less than 850 μm and less than 1000 μm | 22.07 |
| Not less than 710 μm and less than 850 μm | 59.04 |
| Not less than 500 μm and less than 710 μm | 8.99 |
| Not less than 355 μm and less than 500 μm | 0.09 |
| Not less than 250 μm and less than 355 μm | 0.00 |
| Not less than 150 μm and less than 250 μm | 0.09 |
| Less than 150 μm | 0.34 |
| Total | 100.0 |

Comparative Example 1

Ten grams of $^{13}$C uracil and 190 g of D-mannitol (Mannit, a product of Kyowa Hakko Kogyo Co., Ltd.) were placed into a speed kneader (NSK-150, a product of Okada Seiko Co., Ltd.) and mixed, and then, without pulverization, 20 g of purified water was added, followed by kneading. Thereafter, granulation, drying, and particle size regulation by sieving were carried out under the same conditions as in Example 1 to obtain a granular preparation containing 5 wt. % of $^{13}$C uracil. The particle diameter of the thus obtained granular preparation containing 5 wt. % of $^{13}$C uracil was measured using the same method as in Example 1. Table 2 shows the results.

TABLE 2

| Particle Diameter | Proportion (wt. %) |
|---|---|
| 1400 μm or more | 1.24 |
| Not less than 1000 μm and less than 1400 μm | 5.80 |
| Not less than 850 μm and less than 1000 μm | 30.39 |
| Not less than 710 μm and less than 850 μm | 54.87 |
| Not less than 500 μm and less than 710 μm | 6.01 |
| Not less than 355 μm and less than 500 μm | 0.20 |
| Not less than 250 μm and less than 355 μm | 0.10 |
| Not less than 150 μm and less than 250 μm | 0.20 |
| Less than 150 μm | 1.19 |
| Total | 100.0 |

Example 2

Twenty grams of $^{13}$C uracil and 180 g of D-mannitol (Mannit, a product of Kyowa Hakko Kogyo Co., Ltd.) were mixed, placed into a sample mill (KIIWG-1F, a product of Fuji Paudal Co., Ltd.), and mixed and pulverized (at a pulverization rotor speed of 12800 rpm and a sample feed motor speed of about 10 rpm, using a screen with 1-mm diameter punched holes), to prepare a powder material. A 144-g quantity of the obtained powder material was weighed out into a speed kneader (NSK-150, a product of Okada Seiko Co., Ltd.), and 14.4 g of purified water was added, followed by kneading. The resulting wet powder was extruded through an extrusion granulator (Dome Gran DG-L, a product of Fuji Paudal Co., Ltd.) equipped with a dome-shaped die with 1-mm diameter holes, and dried using an air-blow dryer (SPHH-201, a product of Espec Corp.) set at 60° C. Among the particles of the dried preparation, those that passed through a sieve having a mesh size of 1400 μm and did not pass through a sieve having a mesh of 355 μm were obtained as a granular preparation containing 10 wt. % of $^{13}$C uracil.

Comparative Example 2

Twenty grams of $^{13}C$ uracil and 180 g of D-mannitol (Mannit, a product of Kyowa Hakko Kogyo Co., Ltd.) were thoroughly mixed, and placed into a speed kneader (NSK-150, a product of Okada Seiko Co., Ltd.). Twenty grams of purified water was added, followed by kneading. Subsequently, granulation, drying, and particle size regulation by sieving were carried out under the same conditions as in Example 2 to obtain a granular preparation containing 10 wt. % of $^{13}C$ uracil.

Comparative Example 3

Tablets

One hundred grams of $^{13}C$ uracil, 60 g of lactose (a product of H.M.S), 25 g of corn starch (a product of Nihon Shokuhin Kako Co., Ltd.), 10 g of crystalline cellulose (Ceolus PH301, a product of Asahi Kasei Co.), and 4 g of hydroxypropylcellulose (HPC-L fine powder, a product of Nippon Soda Co., Ltd.) were placed into a speed kneader (NSK-150, a product of Okada Seiko Co., Ltd.) and mixed. Forty grams of purified water was then added, followed by kneading. Subsequently, the resulting kneaded powder was granulated using a speed mill (ND-02, a product of Okada Seiko Co., Ltd.) equipped with a screen with 3-mm diameter punched holes, and dried using an air-blow dryer (SPHH-200, a product of Espec Corp.) set at 70° C. The dried granules were sieved through a No. 16 sieve for particle size regulation, and 1 g of magnesium stearate (a product of Taihei Chemical Industrial Co., Ltd.) was added to 199 g of the granules after particle size regulation to obtain granules for tablets. The granules for tablets were compressed into tablets each weighing 200 mg using a single-punch tabletting machine (No. 2B, a product of Kikusui Seisakusho Ltd.) equipped with punches and dies with a diameter of 8 mm and rounded corners.

Example 3

Twenty grams of $^{13}C$ uracil and 180 g of D-mannitol (Mannit, a product of Kyowa Hakko Kogyo Co., Ltd.) were thoroughly mixed, placed into a sample mill (SAM, a product of Nara Machinery Co., Ltd.), and mixed and pulverized (shape of grinding blades: pin-type; rotor speed: 4000 rpm, screen: a screen with 3-mm diameter punched holes), to obtain a powder preparation.

Comparative Example 4

Twenty grams of $^{13}C$ uracil was sieved through a No. 30 sieve to prepare a powder preparation.

Comparative Example 5

Two hundred grams of $^{13}C$ uracil was placed into a sample mill (SAM, a product of Nara Machinery Co., Ltd.) and pulverized under the same conditions as in Example 3, to obtain a powder preparation.

<Evaluation of Properties of Preparations>

Test Example 1 Particle Size Distribution Measurement

The particle size distribution of the powder preparations of Example 3 and Comparative Examples 4 and 5 was measured using a dry particle size distribution measuring apparatus (LDSA-1500A, a product of Tohnichi Computer) under the following conditions: a focal distance of 100 mm, a number of averaging processes of 10, an averaging interval of 5 milliseconds, and an air pressure of 0.4 MPa. From the particle size distribution measured, the particle diameter at 10% (10% D), particle diameter at 50% (50% D), and particle diameter at 90% (90% D) were calculated. Table 3 shows the results.

TABLE 3

|  | 10% D (µm) | 50% D (µm) | 90% D (µm) |
| --- | --- | --- | --- |
| Ex. 3 | 5.74 | 14.95 | 56.58 |
| Comp. Ex. 4 | 6.46 | 75.58 | 235.00 |
| Comp. Ex. 5 | 6.01 | 52.60 | 260.57 |

As shown in Table 3, in the powder preparation of Comparative Example 4, which was obtained by sieving $^{13}C$ uracil alone, and the powder preparation of Comparative Example 5, which was obtained by pulverizing $^{13}C$ uracil alone, the particle diameter was not reduced, indicating an insufficient pulverization effect, whereas in the powder preparation of Example 3, which was obtained by mixing and pulverization, the particle diameter was reduced, demonstrating a sufficient pulverization effect.

Test Example 2

Evaluation of Solubility of Preparations

One hundred milliliters of tap water was added to each of 200-ml beakers at room temperature. Then, while stirring with a magnetic stirrer (RCN-7D, a product of EYELA) at 200 rpm, 2000 mg each of the granular preparations of Example 1 and Comparative Example 1 was added to each beakers, and the time required for the preparations to dissolve was measured by visual observation. Further, three minutes after addition of the granular preparations, the amounts of undissolved residues of the preparations were visually evaluated.

Table 4 shows the results. As is apparent from the results, the preparation of Comparative Example 1 took a long time to dissolve, and a large amount of the preparation remained undissolved; whereas the preparation of Example 1 dissolved in a short time, and only a small amount of the preparation remained undissolved.

TABLE 4

|  | Time Until Dissolution | Undissolved Residue |
| --- | --- | --- |
| Ex. 1 | 1 min 10 sec | Very small amount |
| Comp. Ex. 1 | 3 min or longer | Large amount |

Test Example 3

Evaluation of Solubility of Preparations

Six tablets obtained in Comparative Example 3 were subjected to a disintegration test according to Japanese pharmacopoeia, 14th Edition, General Test Procedures, Disintegration Test. As a result, all the tablets had a disintegration time of 15 minutes or longer.

Test Example 4

Evaluation of Accuracy of Diagnosis of Pyridine Metabolic Capacity Disorder

After orally administering the preparations of Example 2 and Comparative Example 2 to three healthy subjects (Subjects A, B, and C), air expired from the subjects was collected over time and the $^{13}C$ carbon dioxide gas concentration in the expired air was measured using a GC-MS analyzer (ABCA-G, a product of Europa Scientific).

Figure 2:
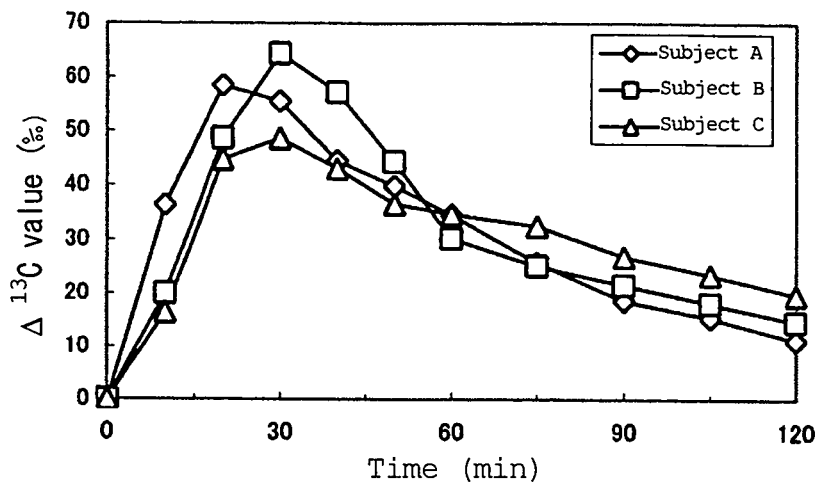
[FIG. 2] A figure comparing the results of observing, over time, the behavior of $^{13}CO_2$ excreted in the expired air of three healthy subjects (Subjects A, B, and C) to whom the granular preparation of Example 2 has been administered.
Figure 3:
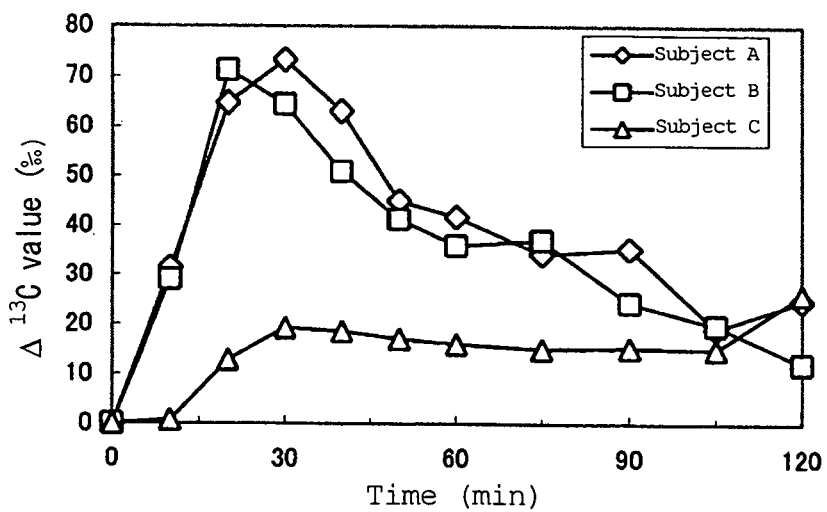
[FIG. 3] A figure comparing the results of observing, over time, the behavior of $^{13}CO_2$ excreted in the expired air of three healthy subjects (Subjects A, B, and C) to whom the granular preparation of Comparative Example 2 has been administered.

FIG. 2 shows the change in $^{13}C$ carbon dioxide gas concentration in the expired air after administration of the preparation of Example 2; and FIG. 3 shows the change in $^{13}C$ carbon dioxide gas concentration after administration of the preparation of Comparative Example 2. In FIGS. 2 and 3, the ordinate indicates $\Delta$ $^{13}C$ values (‰), which are differences between the $\delta$ $^{13}C$ value (‰) ($^{13}CO_2/^{12}CO_2$ concentration ratio) of the expired air collected before administration of the preparation for determining pyrimidine metabolic capacity, and the $\delta$ $^{13}C$ values (‰) of the expired air collected at various periods of time after administration of the preparation. The abscissa indicates the periods (minutes) at which the expired air was collected after administration of the preparation. When the preparation of Comparative Example 2 was administered, the change in $^{13}C$ carbon dioxide gas concentration was small in one of the three subjects, showing variation among the subjects (see FIG. 3). In contrast, when the preparation of Example 2 was administered to the same three subjects, the changes in $^{13}C$ carbon dioxide gas concentration in the subjects were similar to each other, showing only small variation among individuals. These results demonstrate that a pyridine metabolic capacity disorder can be diagnosed rapidly, highly accurately, and with only small variation among individuals, by administering the preparation of Example 2 and diagnosing a pyridine metabolic capacity disorder using, as an index, the $^{13}C$ carbon dioxide gas concentration in the expired air collected 20 to 30 minutes after administration of the preparation (see FIG. 2).

Test Example 5

Diagnosis of Gastric Emptying Capacity

Figure 4:
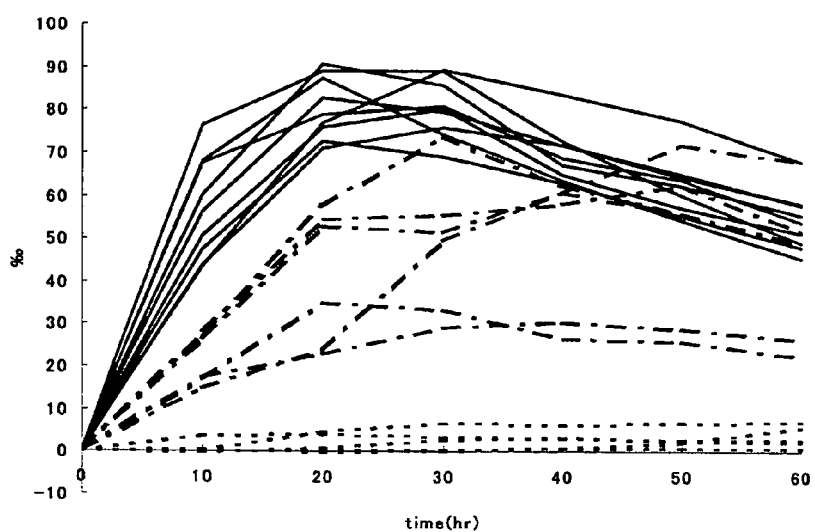
[FIG. 4] A figure showing, over time, the behavior of $^{13}CO_2$ excreted in the expired air of 20 patients suspected of having gastroparesis, to whom the preparation of Example 1 has been administered in Test Example 5.
Figure 5:
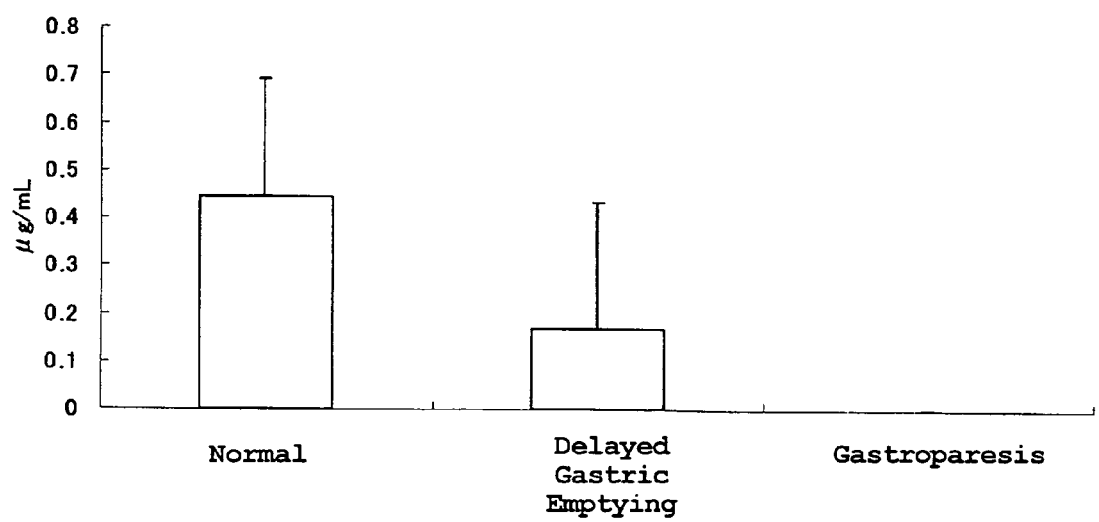
[FIG. 5] A figure showing the plasma 2-$^{13}$C uracil concentration in patients divided into three groups (normal gastric emptying capacity, reduced gastric emptying capacity, and insufficient gastric emptying capacity) based on the results shown in FIG. 4, 20 minutes after administration of the preparation of Example 1.

The preparation of Example 1 was orally administered, at a dose corresponding to 100 mg of 2-$^{13}C$ uracil, to human patients (20 cases) suspected of postoperative gastroparesis, within 20 days after the patients had undergone stomach extraction operations. Air expired from the patients was collected 10, 20, 30, 40, 50, and 60 minutes after administration, and the $^{13}CO_2$ concentrations of the obtained expired air samples, together with those of expired air samples (pre) collected in the same manner before administration, were measured using GC/MS. Subsequently, the amount of change in $^{13}CO_2$ concentration ($\Delta$ $^{13}C$ (‰)) in the expired air was calculated. FIG. 4 shows the results.

As shown in FIG. 4, the expired air test using the preparation of the present invention was able to classify the human patients (20 cases) into those with normal gastric emptying capacity (normal type: solid line), those with reduced gastric emptying capacity (delayed gastric emptying type: broken line), and those with insufficient gastric emptying capacity (insufficient type: dotted line). When the plasma 2-$^{13}C$ uracil concentrations of these patients were measured 20 minutes after administration of the preparation, a reduction in plasma 2-$^{13}C$ uracil concentration was observed in accordance with the gastric emptying capacity, in the patients with reduced gastric emptying capacity (delayed gastric emptying) and in the patients with gastric emptying capacity insufficiency. This demonstrates that the expired air test using the oral preparation of the present invention effectively reflects the gastric emptying capacity.

The invention claimed is:

1. A granular preparation comprising:
   (a) a isotope-labeled compound, selected from the group of uracil and thymine, in which at least one of a carbon atom, an oxygen atom, and a nitrogen atom is labeled with an isotope, and
   (b) a sugar alcohol selected from the group of erythritol, mannitol, xylitol, sorbitol, maltitol, reducing paratinose, and lactitol,
   wherein the granular preparation is produced by
   mixing together the isotope-labeled compound and the sugar alcohol, and
   pulverizing a resulting mixture using a mill to create a powder material,
   wherein a particle diameter at 50% of the powder material is 5 to 20 μm, which is further formulated into a granular preparation, wherein the granular preparation has a mean particle diameter of 1400 μm or less.

2. The granular preparation according to claim 1, which is produced by extrusion granulation of the powder material.

3. A process for producing a granular preparation, the process comprising the steps of:
   (1) mixing together
   (a) a isotope-labeled compound, selected from the group of uracil and thymine, in which at least one of a carbon atom, an oxygen atom, and a nitrogen atom is labeled with an isotope, and
   (b) a sugar alcohol selected from the group of erythritol, mannitol, xylitol, sorbitol, maltitol, reducing paratinose, and lactitol,
   (2) pulverizing a resulting mixture to create a powder material,
   wherein a particle diameter at 50% of the powder material is 5 to 20 μm; and
   (3) formulating the powder material obtained in the above steps into the granular preparation having a mean particle diameter of 1400 μm or less.

4. The process according to claim 3, wherein the granular preparation contains the isotope-labeled compound in a proportion of 5 to 20 wt. %.

5. The process according to claim 3, wherein the isotope-labeled compound is isotope-labeled uracil.

6. A The process according to claim 3, wherein the sugar alcohol is mannitol.

7. The process according to claim 3, wherein the isotope-labeled compound is isotope-labeled uracil and the sugar alcohol is mannitol.

8. The process according to claim 3, wherein the powder material is formulated into a granular preparation by extrusion granulation.

9. The granular preparation according to claim 1, which contains the isotope-labeled compound in a proportion of 5 to 20 wt. %.

10. The granular preparation according to claim 1, wherein the isotope-labeled compound is isotope-labeled uracil.

11. The granular preparation according to claim 1, wherein the sugar alcohol is mannitol.

12. The granular preparation according to claim 1, wherein the isotope-labeled compound is isotope-labeled uracil and the sugar alcohol is mannitol.

* * * * *